United States Patent [19]

Evain et al.

[11] Patent Number: 5,264,612
[45] Date of Patent: Nov. 23, 1993

[54] PROCESS FOR THE PREPARATION OF ARYL-SUBSTITUTED PROPIONIC ACID ESTERS

[75] Inventors: Eric J. Evain; Krishna Raman, both of New Castle County, Del.

[73] Assignee: Himont Incorporated, Wilmington, Del.

[21] Appl. No.: 952,118

[22] Filed: Sep. 28, 1992

[51] Int. Cl.$^5$ .............................. C07C 69/76
[52] U.S. Cl. ...................................... 560/75
[58] Field of Search ........................... 560/75

[56] References Cited

U.S. PATENT DOCUMENTS

| | | | |
|---|---|---|---|
| 3,247,240 | 4/1966 | Meier et al. | 560/75 |
| 3,285,855 | 11/1966 | Dexter et al. | 560/75 |
| 3,364,250 | 1/1968 | Dexter et al. | 560/75 |
| 3,840,585 | 10/1974 | Yamada et al. | 560/75 |
| 3,954,839 | 5/1976 | Dexter et al. | 560/57 |
| 4,228,297 | 10/1980 | Haeberli et al. | 560/75 |
| 4,529,809 | 7/1985 | Irving et al. | 560/75 |
| 4,547,585 | 10/1985 | Tamanaka et al. | 560/75 |
| 4,659,863 | 4/1987 | Burton | 560/75 |
| 5,089,656 | 2/1992 | Yu | 560/75 |

*Primary Examiner*—Paul J. Killos

[57] ABSTRACT

Disclosed is a process for the preparation of aryl-substituted propionic acid esters having the formula:

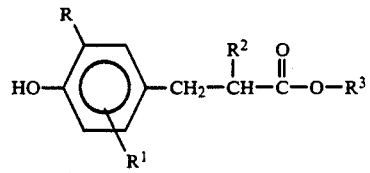

wherein R and $R^1$ are a $C_1$–$C_{12}$ linear or branched alkyl, a $C_5$–$C_{12}$ cycloalkyl, a $C_6$–$C_{12}$ aryl or a $C_7$–$C_{12}$ alkaryl or aralkyl, $R^2$ is hydrogen or a $C_1$–$C_{20}$ linear or branched alkyl and $R^3$ is a $C_1$–$C_{20}$ linear or branched alkyl, a $C_5$–$C_{12}$ cycloalkyl, a $C_6$–$C_{12}$ aryl or a $C_7$–$C_{20}$ alkaryl or aralkyl, and may be the same or different, or $R^1$ is hydrogen, which comprises forming a reaction mixture of a phenol, at least one base catalyst and an acrylate, in the presence of 1,2-dimethoxybenzene, wherein the acrylate is added at once or over a period of time from 5 to 60 minutes at atmospheric pressure. The process results in excellent yields of the desired product with good rates of conversion.

10 Claims, No Drawings

5,264,612

PROCESS FOR THE PREPARATION OF ARYL-SUBSTITUTED PROPIONIC ACID ESTERS

FIELD OF THE INVENTION

This invention relates to a process for the preparation of aryl-substituted propionic acid esters using 1,2-dimethoxybenzene.

BACKGROUND OF THE INVENTION

Aryl-substituted propionic acid esters, such as, methyl 3-(3,5-dialkyl-4-hydroxyphenyl)propionates used as antioxidants for plastics, rubber and other polymers, have been prepared by various methods in the prior art. For example, U.S. Pat. Nos. 3,247,240, 3,285,855 and 3,364,250 disclose preparing methyl 3-(3,5-dialkyl-4-hydroxyphenyl) propionates by reacting a 3,5-dialkyl-4-hydroxybenzene with an acrylate in the presence of a base catalyst, with or without a solvent. The addition of the methyl acrylate in the above processes is over a period of approximately 20 minutes, but the conversion rate is very slow, from about 6 to 72 hours in the presence of a solvent and at least 3 hours without a solvent.

U.S Pat. No. 3,840,855 is directed to a process for producing an alkyl ester of 3-(3,5-di-t-butyl-4-hydroxyphenyl)propionic acid by reacting 2,6-di-t-butylphenol with an alkyl acrylate in the presence of a catalytic amount of a metal hydride with or without a solvent. As in the processes of the above-identified patents, the conversion rate is extremely slow, from about 28 to 42 hours to obtain less than 92% yield.

The process disclosed in U.S. Pat. No. 4,529,809 reacts a stoichiometric excess of an olefinic ester with a sterically hindered phenol in the presence of a base catalyst, with or without a solvent, wherein the reaction time ranged from 11 to 23 hours with reported yields of 32 to 99%.

U.S. Pat. No. 4,547,585 is directed to the formation of methyl-3-(3,5-di-t-butyl-4-hydroxyphenyl)propionate, an intermediate product, by reacting an alkyl acrylate with 2,6-di-t-butylphenol in the presence of an alkaline catalyst and preferably a solvent, such as t-butyl alcohol In this process unreacted acrylate must be removed and the reaction time is from 2 to 10 hours.

In an attempt to minimize the formation of undesirable by-products, U.S. Pat. No. 4,228,297 discloses a process wherein the methyl acrylate is gradually added over a 2 hour period to the phenolic compound in the presence of an alkaline catalyst with or without an aliphatic alcohol or polar aprotic solvent. Preferably an aliphatic alcohol, such as isopropyl alcohol, is used. However, once all of the acrylate is added, an additional 3–4 hours of mixing is necessary to complete the reaction, and then the excess acrylate must be removed before acidifying the reaction mixture. The ester was reported in yields of 84% and 87%.

U.S. Pat. No. 4,659,863 discloses an improved process for preparing methyl esters of hindered phenol derivatives by reacting a hindered phenol with methyl acrylate in the presence of an alkaline catalyst and a reaction rate increasing portion of a solubilizing agent such as DMSO. The methyl acrylate can be added by rapid addition, which is stated to be from 15 to 60 min., to the reaction mixture and unreacted acrylate is removed after completion of the reaction.

U.S. Pat. No. 5,089,656 is directed to a process for preparing aryl substituted propionic acid esters in a shorter period of time with improved conversion, higher purity and minimum formation of undesirable by-products, by removing substantially all of the side-product prior to adding the complexing agent and adding all or substantially all of the acrylate at once to the reaction mixture. The disadvantage of this particular process is that it is highly exothermic. Hence, the temperature of the reaction must be monitored carefully so as to avoid the polymerization of the acrylate. The monitoring of the heat of the reaction is necessary not only to avoid the formation of an undersirable by-product, but more importantly to prevent the reaction from becoming a so-called "acrylate runaway" reaction. Since the acrylate polymerization reaction is also exothermic, it releases additional amounts of heat, which, in turn, causes even more of the acrylate to polymerize. If this additional heat is not dissipated, the reaction can get out of hand and turn into an acrylate "runaway" reaction.

SUMMARY OF THE INVENTION

This invention provides a process for preparing aryl substituted propionic acid esters which avoids the necessity of removing any side-product formed prior to the addition of or in the presence of the DMB complexing agent, has a relatively short reaction time period, has high conversion, and yields a product of high purity.

The process is essentially endothermic as determined by calorimetric measurements using a Contalab bench scale reaction calorimeter (from Contraves Industrial Products Division, Cinncinnati, Ohio). This calorimeter accounts for the energy transfer among (a) the various components of the reactor vessel system (oil jacket, agitator, reactor walls, etc.), (b) the contents of the reaction vessel during the reaction, (c) the condenser system, (if attached), and (d) the materials added, if any, over the period during which the reaction is taking place.

The process for the preparation of aryl-substituted propionic acid esters of the present invention comprises forming a reaction mixture of a phenol, at least one base catalyst and an acrylate, in the presence of 1,2-dimethoxybenzene (DMB) complexing agent. The acrylate may be added all at once or over a period of time ranging from 5 minutes to 60 minutes at atmospheric pressure. However it is preferred to add the acrylate over a period of time ranging from 10 minutes to 40 minutes, most preferably 10 minutes to 30 minutes. Greater than 92% conversion is obtained within 30 minutes after all of the acrylate has been added.

The side-product is not removed prior to or after the addition of the DMB.

As used in the present invention, the term "side-product" refers to those products, individually or collectively, other than the phenoxide intermediate, which results from the reaction of the phenol and the base catalyst. The term "by-product", as used in the present invention refers to those products, individually or collectively, other than the particular aryl-substituted propionic acid esters product desired.

DETAILED DESCRIPTION OF THE INVENTION

In the present invention the process for the preparation of aryl-substituted propionic acid esters of the formula:

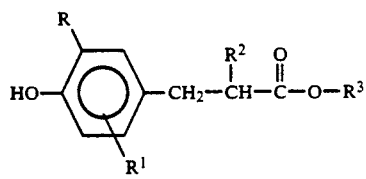

wherein R and $R^1$ are a $C_1$-$C_{12}$ linear or branched alkyl, a $C_5$-$C_{12}$ cycloalkyl, a $C_6$-$C_{12}$ aryl or a $C_7$-$C_{12}$ alkaryl or aralkyl, $R^2$ is hydrogen or a $C_1$-$C_{20}$ linear or branched alkyl and $R^3$ is a $C_1$-$C_{20}$ linear or branched alkyl, a $C_5$-$C_{12}$ cycloalkyl, a $C_6$-$C_{12}$ aryl, or a $C_{7-20}$ alkaryl or aralkyl, and may be the same or different, or $R^1$ is hydrogen comprising (a) forming a reaction mixture of a phenol of the formula:

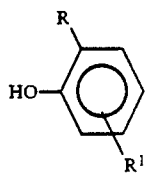

and at least one base catalyst or initiator in an amount sufficient to react with the phenol to form a phenoxide intermediate and side-product(s) in the presence of DMB complexing agent, and (b) adding all of an acrylate of the formula:

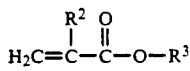

to the reaction mixture of (a) at once or over a period of time from 5 minutes to 60 minutes, said process being conducted at a temperature from 75° to 150° C., preferably 100° to 140° C., most preferably 110° to 140° C.

The phenols useful in this invention have the formula:

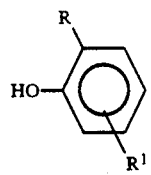

wherein R and $R^1$ are as defined above. Preferably, the phenols are hindered phenols wherein $R^1$ is R as defined above attached to the ring in the position ortho to the hydroxy group. Most preferred are hindered phenols wherein R is a branched alkyl having 4 carbon atoms and $R^1$ is a branched alkyl having 4 carbon atoms attached to the ring in the position ortho to the hydroxyl group, such as 2,6-di-t-butylphenol. Other suitable phenols include 2-methyl-6-t-butylphenol, 2,5-di-t-butylphenol, 2,6-dibenzylphenol, 3,6-di-t-butylphenol, 2,6-diisopropylphenol and the like.

The acrylates useful in the present invention have the formula:

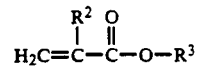

wherein $R^2$ and $R^3$ are as defined above. Suitable examples are methyl acrylate, ethyl acrylate, isopropyl acrylate and methyl methacrylate. Preferred is methyl acrylate.

The acrylate is used in amount of from 1 to 1.2 moles per mole of phenol employed in the present invention. The preferred range is from 1.05 to 1.15 moles of acrylate per mole of phenol.

The base catalyst or initiator used in the present invention is an alkali metal catalyst such as alkali metal hydroxides, alkali metal alkoxides, alkali metal amides and alkali metal alkyl amides. Alkali metals for the base catalyst include lithium, sodium and potassium. Examples of the base catalyst or initiator used in the present invention are lithium hydroxide, sodium hydroxide, potassium hydroxide, potassium methoxide, sodium methoxide, lithium methoxide, potassium ethoxide, sodium ethoxide, lithium ethoxide, potassium t-butoxide, sodium t-butoxide, n-butyllithium, phenyl potassium, phenyl sodium, potassium amide, lithium diisopropyl amide and mixtures thereof. Preferred are potassium t-butoxide and sodium methoxide and most preferred is sodium methoxide. A suitable amount of base catalyst or initiator used in the process of this invention is from about 5 to 100 mole percent based on the amount of phenol added. Preferably, the base catalyst is used in an amount of from about 5 to 30 mole percent and most preferably, from 5 to 20 mole percent based on the amount of phenol reacted.

In accordance with the present invention the reaction is carried out in the presence of DMB complexing agent which is believed to increase the nucleophilicity of the phenoxide by complexing with the metal ion of the base catalyst. An effective amount of the DMB complexing agent used in the present invention is from 5 to 70 mole percent per mole of phenol, preferably 10 to 40 mole percent.

According to the process of this invention, a reaction mixture of the phenol and at least one base catalyst is formed in the presence of the DMB complexing agent. The reaction mixture is heated to about 75° to 150° C., preferably 100° C. to 140° C., wherein a phenoxide intermediate and side-product are formed. Then all of the acrylate is added at once or over a period from 5 minutes to 60 minutes, preferably from 10 to 40 minutes, to the reaction mixture which is maintained at a temperature of 110° to 150° C., preferably 110° to 140° C., most preferably 130° to 140° C. Addition of the acrylate over a period of time is preferred. Once the addition is complete, the reaction kept at a temperature from 130° to 140° C., preferably 135° C. to 140° C. for about 30 to 120, generally 30 to 60 minutes, until the reaction is complete.

The reaction mixture is then neutralized with an acid and the product is recovered. Such acids include glacial acetic acid or 3 to 10% diluted hydrochloric acid, sulfuric acid or formic acid. Preferred is glacial acetic acid.

The percent conversion is determined on an aliquot sample (approx. 1 ml) of the acidified reaction mixture by gas chromatograph analysis using a Hewlett Packard HP5980 gas chromatograph.

The temperature range for carrying out the reaction is from about 75° C. to 150° C., preferably from 110° to 140° C.

The present invention will be illustrated in greater detail with reference to the examples of the invention set forth below.

EXAMPLE 1

To a 1000 ml reaction vessel, equipped with a twin-blade axial flow impeller mechanical agitator, a nitrogen sparge tube, a thermometer, and external oil jacket and a reflux condenser connected to a cold trap and a mercury bubbler, are charged, under nitrogen atmosphere, 206.3 g (1 mole) 2,6-di-t-butylphenol and 30.0 g (217.0 mM) DMB. Potassium t-butoxide (5.61 g, 50.0 mM) is then added and stirring commenced with the agitator set at 750 rpm. The reaction mixture is heated to 110° C. Next 94.63 g (1.10 mole) methyl acrylate is added subnatantly to the reaction mixture over 30 minutes, while stirring. The reaction is then continued for about 120 minutes while maintaining the temperature of the reaction mixture at 140° C. The contents of the reaction vessel is then cooled to 110° C. and 3 ml (0.05 mole) glacial acetic acid is added. An aliquot sample (about 1 ml) is removed from the acidified reaction mixture for the determination of the percent conversion of the 2,6-di-t-butylphenol to the methyl-3-(2,6-di-t-butyl-4-hydroxyphenyl)propionate product (99% conversion). The reaction mixture is then filtered and the filtrate distilled. 274.8 g (94% yield) of the product is obtained which has a purity of greater than 99% by HP5980 gas chromatograph assay.

EXAMPLE 2

The procedure and ingredients of Example 1 are used except that sodium methoxide in methanol (9.0 g of a 30% methanol solution, 0.05 mole sodium methoxide) is added instead of the potassium t-butoxide. 269.0 g (92% yield) of methyl-3-(2,6-di-t-butyl-4-hydroxyphenyl)propionate is obtained with a conversion of 99%. Gas chromatograph assay of the product shows a purity of greater than 99%.

EXAMPLE 3

To a 1000 ml reaction pressure vessel, equipped with a standard flat blade agitator, a thermometer, and an external oil jacket are charged, under a nitrogen atmosphere and at room temperature, 212.8 g (1.031 mole) 2,6-di-t-butylphenol and 31.0 g (0.22 mole) DMB. The contents are heated to 75° C. Sodium methoxide (11.8 ml of a 25 wt. % methanol solution, 51.6 mM sodium methoxide) is then added via a syringe and stirring commenced with the agitator set at 1000 rpm. The reaction mixture was heated to 80° C. and 97.6 g (1.134 mole) methyl acrylate is added substantially all at once, while stirring and heating to 140° C. over 30 minutes. The internal pressure of the reaction vessel did not rise above 5 psig. The reaction is then continued for about 120 minutes while maintaining the temperature of the reaction mixture at 140° C. The contents of the reaction vessel is then cooled to 110° C. and 5 ml (0.09 mole) glacial acetic acid is added. An aliquot sample (about 1 ml) is removed and a 93% conversion is determined.

The aryl-substituted propionic acid esters produced by the process of the present invention are obtained in excellent yields, substantially free of undesirable by-products and in a short period of time. The process of this invention can be conducted as a batch, semi-batch or continuous process. The resulting esters may be used for stabilization of organic materials or as chemical intermediates to the production of known antioxidants for plastics, rubber and other polymers.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

We claim:

1. A process for the preparation of aryl-substituted esters of the formula:

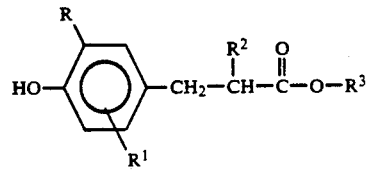

wherein R and $R^1$ are a $C_1$–$C_{12}$ linear or branched alkyl, a $C_5$–$C_{12}$ cycloalkyl, a $C_6$–$C_{12}$ aryl or a $C_7$–$C_{12}$ alkaryl or aralkyl, $R^2$ is hydrogen or a $C_1$–$C_{20}$ linear or branched alkyl and $R^3$ is a $C_1$–$C_{20}$ linear or branched alkyl, a $C_5$–$C_{12}$ cycloalkyl, a $C_6$–$C_{12}$ aryl, or a $C_1$–$C_{20}$ alkaryl or aralkyl, and may be the same or different, or $R^1$ is hydrogen, comprising forming (a) a reaction mixture of a phenol of the formula:

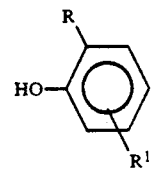

wherein R and $R^1$ are as defined above, at least one base catalyst or initiator, in the presence of 1,2-dimethoxybenzene and (b) adding an acrylate of the formula:

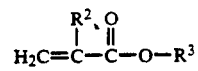

wherein $R^2$ and $R^3$ are as defined above, all at once or over a period of 5 to 60 minutes to said reaction mixture at atmospheric pressure, wherein (a) and (b) are conducted at a temperature from about 75° C. to 150° C., and once the addition (b) is complete, maintaining the temperature at from 130° C. to 140° C. for about 30 to 120 minutes.

2. A process according to claim 1, wherein said acrylate is selected from the group consisting of methyl acrylate, ethyl acrylate, methyl methacrylate or isopropyl acrylate.

3. A process according to claim 1, wherein said phenol is 2,6-di-t-butylphenol, 2-methyl-6-t-butylphenol, 2,5-di-t-butylphenol, 2,6-diphenylphenol or 2,6-di-benzylphenol.

4. A process according to claim 1, wherein said base catalyst is selected from the group consisting of alkali metal alkoxides, alkali metal hydroxides, alkali metal amides, alkali metal alkyl amides and mixtures thereof.

5. A process according to claim 4, wherein said base catalyst is an alkali metal alkoxide.

6. A process according to claim 5, wherein the alkali metal alkoxide is sodium methoxide.

7. A process according to claim 1, wherein said base catalyst is present in the amount of from 5 to 100 mole percent per mole of phenol.

8. A process according to claim 7, wherein said base catalyst is present in the amount of from 5 to 20 mole percent per mole of phenol.

9. A process according to claim 1, wherein said DMB complexing agent is present in the amount of from 5 to 70 mole percent per mole of phenol.

10. A process according to claim 9, wherein said DMB complexing agent is used in the amount of from 10 to 40 mole percent per mole of phenol.

* * * * *